United States Patent
Kunz et al.

(10) Patent No.: US 7,524,798 B2
(45) Date of Patent: *Apr. 28, 2009

(54) USE OF A POLYESTER COMPOSITION AS A HYDRAULIC FLUID

(75) Inventors: Markwart Kunz, Worms (DE); Jörg Kowalczyk, Eisenberg/Steinborn (DE); Alireza Haji Begli, Ramsen (DE); Rainer Kohlstrung, Schwetzingen (DE); Manfred Harperscheid, Römerberg (DE); Angela Kesseler, Oberhausen (DE); Rolf Luther, Speyer (DE); Theo Mang, Weinheim (DE); Christian Puhl, Grünstadt (DE); Helena Wagner, Cologne (DE)

(73) Assignee: Sudzucker Aktiengesellschaft Fuchs Petrolub AG, Manheim/Ochsenfurt (DE)

( * ) Notice: Subject to any disclaimer, the term of this patent is extended or adjusted under 35 U.S.C. 154(b) by 760 days.

This patent is subject to a terminal disclaimer.

(21) Appl. No.: 10/486,149

(22) PCT Filed: Jul. 22, 2002

(86) PCT No.: PCT/EP02/08140

§ 371 (c)(1),
(2), (4) Date: Feb. 6, 2004

(87) PCT Pub. No.: WO03/014269

PCT Pub. Date: Feb. 20, 2003

(65) Prior Publication Data

US 2005/0032653 A1    Feb. 10, 2005

(30) Foreign Application Priority Data

Aug. 7, 2001    (DE) ................ 101 38 686

(51) Int. Cl.
*C10M 169/04* (2006.01)
*C07C 53/00* (2006.01)
(52) U.S. Cl. .................. 508/220; 508/216; 554/227
(58) Field of Classification Search ............... 508/216, 508/220; 554/227
See application file for complete search history.

(56) References Cited

U.S. PATENT DOCUMENTS

| 2,700,022 | A |   | 1/1955 | Lindstrom et al. |
|---|---|---|---|---|
| 3,468,701 | A |   | 9/1969 | Hughes |
| 3,959,159 | A | * | 5/1976 | Coleman ............... 508/467 |
| 4,144,183 | A |   | 3/1979 | Koch et al. |
| 5,102,567 | A |   | 4/1992 | Wolf |
| 5,773,391 | A |   | 6/1998 | Lawate et al. |
| 6,051,539 | A | * | 4/2000 | Kodali et al. .......... 508/491 |
| 6,402,983 | B1 | * | 6/2002 | Abe et al. .............. 252/77 |

FOREIGN PATENT DOCUMENTS

| EP | 0 482 325 |   | 4/1992 |
|---|---|---|---|
| EP | 0 572 198 |   | 12/1993 |
| EP | 0 879 872 |   | 11/1998 |
| GB | 793 141 |   | 4/1958 |
| GB | 793141 |   | 4/1958 |
| GB | 793141 | * | 9/1958 |
| JP | 01-287060 |   | 11/1989 |
| JP | 6-65274 |   | 3/1994 |
| JP | 8-67690 |   | 3/1996 |
| JP | 10-17588 |   | 1/1998 |
| JP | 10-511711 |   | 11/1998 |
| JP | 2000-169871 |   | 6/2000 |
| JP | 2000-514470 |   | 10/2000 |

OTHER PUBLICATIONS

Aslam M., Torrence, G.P., and Zey, E.G, Esterification, in Kirk-Othmer Encyclopedis of Chemical Technology, vol. 10, John Wiley & Sons, 1994, p. 471-496.*
Lawson, Sugar Alcohols, in Kirk-Othmer Encyclopedia of Chemical Technology, John Wiley & Sons, 1997, p. 8.*
International Search Report.

* cited by examiner

*Primary Examiner*—Glenn Caldarola
*Assistant Examiner*—Jim Goloboy
(74) *Attorney, Agent, or Firm*—Ostrolenk, Faber, Gerb & Soffen, LLP

(57) ABSTRACT

The present invention relates to the use of polyesters which consist of at least one carbohydrate and at least one carboxylic acid, and mixtures thereof, as a hydraulic fluid.

23 Claims, No Drawings

USE OF A POLYSTER COMPOSITION AS A HYDRAULIC FLUID

The present invention relates to the use of polyesters which consist of at least one carbohydrate and at least one carboxylic acid, and mixtures thereof, as a hydraulic liquid or hydraulic fluid.

Hydraulic drives enable the transfer of large forces using relatively simple elements and the stepless variation of working speeds, and hydraulic energy transport take place between the generating section, the pumps and the motor section, the hydraulic motors or turbines, via a hydraulic fluid. Depending on the mode of action, a distinction is drawn between hydrostatic and the less common hydrokinetic drives. The hydrostatic drive works by the principle of volume displacement in enclosed, changing spaces. The pump displaces a certain volume of hydraulic fluid per stroke or revolution against a pressure existing in the flow (hydraulic motor). The hydrokinetic drive functions by the principle of inertia by deflecting a mobile hydraulic fluid mass in blade cascades arranged in rotational symmetry (turbines).

In the fulfillment of the function of hydraulic systems, the hydraulic fluid is of substantial importance. The fundamental objects of the hydraulic fluid are the transfer of output or signals to hydraulic systems. Hydraulic oils or hydraulic fluids therefore refer to those liquid substances or mixtures which are suitable for energy transfer in hydrostatic or hydrokinetic (hydrodynamic) systems. In addition to energy transfer, hydraulic fluids should ensure sufficient lubrication of lubrication points and the protection of the components of the hydraulic drive from corrosion, and also remove heat from the system. Irrespective of the different conditions in different hydraulic systems, the hydraulic pressure medium always has to guarantee trouble-free functioning of the individual hydraulic components. In addition to appropriate flow behavior and good compressibility, i.e. low volume and pressure variation under pressure, for the disruption-free transport of energy, hydraulic fluids therefore have to have very good sliding properties for lubrication, high specific heat for cooling, good compatibility with the system materials and corrosion protection properties.

The different hydraulic machines and units have highly differing operating conditions, for example extremely high or extremely low temperatures. Depending on the application, the hydraulic fluids therefore have to have not only the aforementioned general functional properties, but also application-specific properties which may be very different from case to case. For example, hydraulic fluids for hydraulic systems of airplanes have to have particularly good low temperature properties. In fire-endangered hydraulic units, for example in bituminous coal mining, low-flammability hydraulic fluids in particular are used. The brake fluids which likewise belong to the hydraulic fluids have to be, for example, cold-, heat- and aging- and also oxidation-resistant, noncorrosive and not have any effect on rubber.

The specific characteristic data of hydraulic liquids which are of interest especially from an application point of view include viscosity-temperature behavior, viscosity-pressure behavior and the determination of the density-temperature dependence. The change in the viscosity with the pressure or the temperature is well known for many conventional hydraulic fluids, in particular from the group of the mineral oils. With increasing temperature, for example, mineral oils used as a hydraulic liquid have distinctly lower viscosities than at lower temperatures. When the viscosity goes below a lower minimum as a result of excessively high temperatures, this results in mixed or solid state friction in hydraulic components, which increases the overall friction and intensifies the wear. In contrast, excessively high viscosities are to be avoided in particular from an energetic point of view.

Like other hydraulic components, the hydraulic medium also undergoes aging during the time, which manifests itself in a change in the characteristic physical and chemical parameters. For example, the hydraulic medium loses its good tribological properties, and its original object, namely the protection of the components from corrosion, becomes reversed, which may result in a corrosive attack on the components of the hydraulic drive.

Every year, about 160 000 metric tons of hydraulic fluid products are used in Germany, about 40% of the total amount of hydraulic fluid being accounted for by mobile applications and 60% by stationary applications. These are in particular the hydraulic oils H (aging-resistant without active additives), HL (with active ingredients for increasing the aging resistance and the corrosion protection), HLP (additionally with active ingredients for preventing wear in the mixed friction range) and HVLP (additionally -with active ingredients for improving the viscosity-temperature behavior). The hydraulic fluid products also include the low-flammability hydraulic fluids which are used in particular in fire-endangered hydraulic units and for which a distinction is drawn between the types HFA (oil-in-water emulsions), HFB (water-in-oil emulsions), HFC (aqueous polymer solutions, for example of polyglycols) and HFD (anhydrous fluids, for example phosphoric esters, silicic esters, silicones, halohydrocarbons and others). Likewise included are brake fluids which, in hydraulic brake systems of vehicles, serve to transmit the brake pressure and consist conventionally of glycols, glycol ethers and/or polyalkyl glycols.

According to an inquiry of the German Federal Environmental Office (1997), 73.2% of the hydraulic fluids used in the industrial sector are collected again after use and fed to recycling. This means that about 30% of all hydraulic fluids remain in the environment. A large portion of these products gets into the environment, into soils or groundwater and surface water as a result in particular of leaks from hydraulic systems or as a result of the loss of drops, for example when hydraulic hoses are changed in excavators. However, as a consequence of their chemical composition, many hydraulic fluids are hardly decomposed, or are decomposed only very slowly, by the natural systems of the environment, for example microorganisms. This constant contamination of the soil, the groundwater and surface water with hydraulic fluids therefore leads in the long term to considerable risks for flora, fauna and humans.

In view of the risks to the environment which arise in particular from hydraulic fluids based on mineral oils, efforts have been made for some time to develop biodegradable hydraulic oils. For example, hydraulic oils have been developed which are based on vegetable oils such as rapeseed oil or sunflower oil and derivatives thereof. Although these products based on natural, in particular vegetable, oils offer the advantage of relatively rapid biodegradability, they frequently do not have, or have only to an insufficient extent, the properties required for use as a hydraulic fluid, such as viscosity-temperature behavior, long-term cold stability, aging stability, etc.

Further renewable raw materials such as sugar and starch have hitherto remained unused for the application as a hydraulic fluid and their potential as a polyol constituent for synthetic esters is virtually unresearched. However, their availability makes such raw materials very attractive, especially because their natural origin gives rise to advantages with regard to rapid biodegradability and environmental compatibility. The prior art merely discloses a few applications of sugar compounds in the lubricants field, but not in the hydraulic fluids field.

EP 0 879 872 A1 discloses biodegradable, nontoxic lubricant oil formulations which consist of an ester of a sugar and of a fatty acid. The polyol constituent of the polyester may include a sugar, sugar alcohol or a mixture thereof. The nontoxic lubricant oil formulation described is intended to find use in particular in aggregates which are used in the agricultural and food industry, or in the cosmetics or pharmaceutical industry.

EP 0 572 198 A1 describes lubricant compositions which may likewise be used for machines for producing foods. The compositions comprise a mixture of a first ester of a medium-length saturated fatty acid with glycerol (component A) and of a second ester of a carboxylic acid with sucrose.

DE 42 29 383 C2 describes an edible lubricant with the addition of lubricity-improving esters of fatty acids and higher alcohols. The additives for improving the lubricity consist of at least two esters of edible alcohols having at least two alcohol groups. Useful alcohols include, for example, glycerol, pentaerythritol, arabitol, mannitol and sorbitol.

The technical problem on which the present invention is based is thus to provide synthetic esters whose structure is based fully on renewable raw materials and which are obtainable in particular using low molecular weight sugars and from fatty acids which can be isolated from vegetable sources as base fluids for hydraulic fluids, these synthetic esters on the one hand having the required performance properties such as oxidation and aging stability, thermal stability, suitable viscosity-temperature behavior, suitable viscosity-pressure behavior, etc., and, on the other hand, as a consequence of their natural origin, being rapidly biodegradable and thus environmentally compatible to a high degree.

The invention solves the technical object on which it is based by the use of a rapidly biodegradable composition comprising at least one polyester or at least one polyester derivative and a polyester mixture, the polyester having been formed from a carbohydrate, each of which has been esterified with at least one carboxylic acid, at least one carboxylic acid derivative or a mixture thereof, as a hydraulic oil.

The polyester or sugar ester present in the composition is obtained by chemically joining the carbohydrate and the carboxylic acid or the carboxylic acid derivative or a mixture thereof. Most sugar esters belong to the class of the nonionic surfactants. Owing to their amphiphilic character, their particular readiness to biodegrade and their good surface properties, these sugar esters have hitherto been used mainly in the foods industry, cosmetics and pharmaceuticals. The present invention thus provides for the first time the use of such sugar esters as the base fluid of hydraulic oils. The invention provides in particular that the polyester or sugar ester has a structure based fully on renewable raw materials, in particular indigenous raw materials, for example vegetable oils and fats. In other words, all constituents which are used to synthesize the polyester used as a hydraulic fluid in accordance with the invention, i.e. both carbohydrate constituent and carboxylic acid constituent, are obtained from renewable, in particular vegetable, raw materials, for example vegetable oils and fats. The polyester having such a structure may then, when it gets into the environment, for example into soils or surface water or groundwater, be rapidly degraded by natural systems such as microorganisms as a consequence of its natural constituents.

Investigations of the applicant of the present invention have shown that the polyesters used in accordance with the invention have outstanding hydraulic fluid properties, for example viscosity behavior which is exquisitely suitable for this field of application, load-bearing capability, wear behavior, very good air release capability and very good oxidative aging stability.

In connection with the present application, the term "use as a hydraulic oil", "use as a hydraulic fluid" or "use as a hydraulic liquid" means that a substance or substance mixture which is either liquid by nature or in its liquid form after dissolution in a liquid medium has properties which enable use of the substance in hydrostatic or hydrokinetic (hydrodynamic) systems for energy transfer. According to the invention, "use as a hydraulic fluid" means in particular the use as a base fluid for hydraulic oils and does not rule out the addition of further conventionally used additives for hydraulic oils, such as phenolic and/or aminic antioxidants, phosphorus/sulfur extreme pressure/antiwear additives, corrosion inhibitors, foam inhibitors and other performance-improving additives.

A preferred embodiment of the invention therefore provides for the use of a carbohydrate ester composition comprising at least one polyester or at least one polyester derivative or a mixture thereof, the polyester consisting of a carbohydrate and at least one carboxylic acid, a derivative thereof or a mixture thereof as a base fluid for hydraulic oils, the composition additionally comprising additives which are typical for hydraulic oil and are selected from the group consisting of antioxidants, high-pressure and wear additives, corrosion inhibitors, foam inhibitors and viscosity regulators.

In connection with the present invention, "rapidly biodegradable" means that the polyester composition used in accordance with the invention is rapidly degraded by the biological systems of the environment, in particular microorganisms such as bacteria and fungi which are present in the environment. The resulting low molecular weight degradation products also do not constitute any environmental pollution, either because they are already naturally occurring substances which are nontoxic for flora and fauna and are thus environmentally compatible, or because the decomposition products may be degraded by successive biological systems, in particular further microorganisms, to such naturally occurring nontoxic substances. The present invention thus provides that the natural degradation of the composition used as a hydraulic fluid in accordance with the invention leads substantially to products which are safe for organisms such as animals and humans.

In connection with the invention, "at least one polyester" means that the composition used in accordance with the invention as a base fluid for hydraulic oils contains at least one polyester, but may contain a plurality of different polyesters. "At least one carbohydrate" means that the different polyesters present in the composition contain at least one carbohydrate radical, and this carbohydrate may be esterified with a carboxylic acid, but also with different carboxylic acids. However, the polyesters used in accordance with the invention may also include a plurality of different carbohydrate constituents which may be esterified either with only one carboxylic acid or one carboxylic acid derivative or with different carboxylic acids and/or carboxylic acid derivatives. "At least one carboxylic acid or at least one derivative thereof" means that a carbohydrate radical present in the composition may be esterified with at least one carboxylic acid radical or at least one derivative of a carboxylic acid, or else with different carboxylic acids or different carboxylic acid derivatives or a mixture thereof.

The present invention provides in particular that the carbohydrate constituent of the polyester composition used in accordance with the invention may be isolated directly from renewable raw materials, in particular indigenous vegetable raw materials, or may be prepared inexpensively from natural products in few industrial steps. In a preferred embodiment of the invention, the carbohydrate is a monosaccharide, disaccharide, trisaccharide, a sugar alcohol derived therefrom, a starch hydrolyzate, fructooligosaccharides, a hydrogenated product thereof, a mixture thereof or dehydrated intermediates of the carbohydrate, for example sorbitan, dianhydrosorbitol, etc.

In a preferred embodiment of the invention, the carbohydrate is xylose, arabinose, ribose, maltose, lactose, sucrose, raffinose, glucose, mannose, galactose, sorbose, fructose, isomaltulose, trehalulose, lactitol, maltitol, hydrogenated maltotriose, sorbitan, xylitol, sorbitol, mannitol, erythritol, arabitol, 6-O-α-D-glucopyranosyl-D-sorbitol (1,6-GPS), 1-O-α-D-glucopyranosyl-D-sorbitol (1,1-GPS), 1-O-α-D-glucopyranosyl-D-mannitol (1,1-GPM), isomalt, or a mixture thereof. In a particularly preferred embodiment of the invention, the sugar alcohol used as a starting substance for preparing the polyester used in accordance with the invention is sorbitol.

A further preferred embodiment of the invention provides that the polyester contains, as the acid constituent, an unbranched and/or branched saturated or unsaturated monocarboxylic acid, dicarboxylic acid, tricarboxylic acid, a derivative thereof or an isomer thereof, each of which may be directly isolated from renewable raw materials, in particular indigenous vegetable raw materials, for example vegetable oils and fats, or may be prepared from natural products inexpensively in few industrial steps and is therefore particularly efficiently biodegradable.

The chain length of the acid constituent has a significant influence on the properties of the polyester, for example viscosity-temperature behavior, viscosity-pressure behavior and material compatibility. The present invention therefore provides that the carbohydrate constituent of the composition used in accordance with the invention has been esterified in particular with monocarboxylic acid, preferably a $C_2$-$C_{24}$-monocarboxylic acid, more preferably a $C_4$-$C_{18}$-monocarboxylic acid.

A particularly preferred embodiment of the invention therefore relates to the use of a composition in which the carbohydrate has been esterified with acetic acid, butyric acid, isobutanoic acid, valeric acid, isovaleric acid, caproic acid, enanthic acid, caprylic acid, 2-ethylcaproic acid, pelargonic acid, capric acid, isostearic acid, lauric acid, myristic acid, myristoleic acid, palmitic acid, palmitoleic acid, stearic acid, oleic acid, elaidic acid, ricinoleic acid, linoleic acid, linolenic acid, eleostearic acid, arachic acid, behenic acid or erucic acid or a mixture of these acids.

The present invention also provides that the polyester which is to be used as a hydraulic oil in accordance with the invention also contains, as the acid component, a derivative of a carboxylic acid such as an anhydride, mixed anhydride, an alkyl ester or a carbonyl chloride. Anhydrides are the products of an acid, for example a carboxylic acid, which are obtainable, for example, by dehydration. The loss of water from two different acids may result in mixed anhydrides. Alkyl esters may be prepared by an acid-catalyzed reaction of carboxylic acids with alcohols.

A further preferred embodiment of the invention therefore relates to compositions in which the open-chain and cyclic D-sorbitol and D-mannitol derivates have been esterified with carboxylic acid derivatives, for example anhydrides, mixed anhydrides, alkyl esters, in particular carbonyl chlorides.

In a further preferred embodiment, the sugar alcohol derivatives may also have been esterified with isomers of carboxylic acids such as cis/trans isomers within the structure or at geometric positions. Isomers are compounds having the same empirical, but different structural, formulae. Cis/trans isomers are stereoisomers which feature a different atom arrangement in three-dimensional space, in particular a different arrangement of the substituents. Stereoisomers therefore differ in the configuration and/or the confirmation. A particularly preferred embodiment of the invention therefore relates to the use of a composition in which the carbohydrate has been esterified with a derivative or an isomer of monocarboxylic acid.

A preferred embodiment of the invention provides that the carbohydrate ester intended for use as a hydraulic fluid has such a degree of esterification that at least 75% of all free hydroxyl groups of the carbohydrate have been esterified. A particularly preferred embodiment of the invention provides that all free hydroxyl groups of the carbohydrate have been esterified with at least one carboxylic acid, at least one carboxylic acid derivative or a mixture thereof.

A further embodiment of the invention relates to the use of a carbohydrate ester as a hydraulic oil, wherein the polyester can be prepared by esterifying or transesterifying the carbohydrate or a mixture comprising a plurality of different carbohydrates, in solvents or without solvent, in the presence of a catalyst. The products which are intended for use as a hydraulic oil or hydraulic fluid may thus be prepared in known organic solvents such as toluene, DMSO, pyridine, DMF and the like, but also without solvent, by esterifying or transesterifying the carbohydrate (polyol) mixture with the appropriate reagents with the addition of suitable catalysts.

The present invention provides in particular that the products used as hydraulic fluids in accordance with the invention are prepared using transition metal compounds of in particular Sn, Ti or Zn/Cu, for example salts, oxides, alkyls, etc., mineral acids such as HCl, $H_2SO_4$ or $H_3PO_4$, organic acids such as p-toluenesulfonic acid, methanesulfonic acid or sulfosuccinic acid, acidic ion exchangers, alkaline metal salts such as hydroxides, carbonates, methoxides, ethoxides of, for example, sodium or potassium, zeolites or mixtures thereof.

Particular preference is given in accordance with the invention to using p-toluenesulfonic acid or a tin oxalate catalyst as the catalyst.

The present invention provides that the carbohydrate esters intended for use as a hydraulic fluid are prepared by transesterifying or esterifying in one or more solvents or without solvent. Particular preference is given in accordance with the invention to organic solvents such as toluene, DMSO, pyridine or DMF.

The present invention provides that the carbohydrate esters intended for use as a hydraulic fluid are prepared by a transesterification or esterification at a temperature of from 120° C. to 280° C. Particular preference is given to using carbohydrate esters which are prepared at an esterification or transesterification temperature of from 160° C. to 250° C.

The ratio of the carbohydrate and acid starting constituents, in particular the ratio of hydroxyl groups to carboxylic acid groups, in the esterification or transesterification has a decisive influence on the degree of esterification of the resulting carbohydrate esters. The amount of the acid constituents to be used in the reaction, based on the amount of the carbohydrate constituent used, depends upon how many free hydroxyl groups the carbohydrate used as a starting material has. The present invention provides in particular that the ratio of hydroxyl groups to carboxylic acid groups is from 1:1 to 1:10. A preferred embodiment of the present invention therefore relates to the use of carbohydrate esters in whose preparation the ratio of hydroxyl groups to carboxylic acid groups of the starting constituents is from 1:1 to 1:10. Particular preference is given to using carbohydrate esters in whose preparation the starting ratio of hydroxyl groups to carboxylic acids groups of the carbohydrate and acid starting constituents is from 1:1.5 to 1:7.

The reaction time used for the esterification or transesterification also has a decisive influence on the degree of esterification of the resulting products. The present invention provides that the duration of the esterification or transesterification of the carbohydrates with carboxylic acids is from 2 to 36 hours, more preferably from 4 to 26 hours, most preferably from 8 to 10 hours. A preferred embodiment of the present invention thus relates to the use of carbohydrate esters whose preparation by esterifying or transesterifying a carbohydrate with a carboxylic acid or a carboxylic acid derivative takes from 2 to 36 hours, more preferably from 4 to 26 hours, most preferably from 8 to 10 hours.

The inventively preferred reaction conditions for esterifying or transesterifying carbohydrates to prepare the polyesters used in accordance with the invention preferably include the following parameters: use of a stirred reactor, although the esterification may also be carried out in accordance with the invention in from 2 to 5 stages in a stirred tank battery, removal of water during the reaction by rectification or azeotropic rectification, carrying out the reaction in an organic solvent, for example toluene, DMF or ether, or without solvent, a reaction time of from 2 to 36 hours, preferably from 8 to 26 hours, and carrying out the reaction in the presence of a catalyst, the amount of catalyst based on the total amount being 0.05-10% by weight, preferably 0.1-5% by weight. The carbohydrate and acid starting substances, based on the monomer units, are preferably in a ratio of from 1:1 to 1:10, more preferably in a ratio of from 1:1.5 to 1:7. The reaction is preferably effected under a reduced pressure of from 300 to 10 mbar.

The carbohydrate esters intended in accordance with the invention for use as hydraulic fluids or hydraulic oils have outstanding physicochemical properties which predestine them in particular for this field of application. The carbohydrate esters used in accordance with the invention have, for example, a kinematic viscosity of 40° C. of from about 20 to 120 $mm^2/s$. Investigations have also shown that they have an excellent long-term cold stability, since they are still free-flowing after several days at −25° C. Their outstanding oxidative aging stability can be demonstrated in the turbine oil stability test.

A preferred embodiment of the invention therefore relates to the use of carbohydrate ester compositions which have a kinematic viscosity of from 20 to 120 $mm^2/s$ as hydraulic fluids. A further embodiment of the invention relates to the use, as hydraulic fluids, of carbohydrate esters which have such a long-term cold stability that they are still free-flowing after three days at a temperature of −25° C. Yet another preferred embodiment of the invention relates to the use, as a base fluid for hydraulic oils, of a carbohydrate ester composition which has a pour point lower than −25° C. The present invention also provides that the carbohydrate ester compositions which are used as hydraulic fluids have a load-bearing capability of at least load stage 10 in the FZG A/8.3/90 test method. The present invention further provides that carbohydrate ester compositions are used, as hydraulic fluids, which require more than 1 800 hours in the turbine oil stability test without the addition of water until an acid number of 2 mg KOH/g has been attained.

The present invention is illustrated in detail by the examples which follow.

EXAMPLE 1

Preparation of a sugar ester by esterifying D-sorbitol and D-mannitol with caprylic anhydride (batchwise variant)

In a stirred reactor, 250 g of a 1:1 mixture of D-sorbitol and D-mannitol were dehydrated at 155° C. for 1.25 hours in the presence of 0.8 g of p-toluenesulfonic acid. After 1.86 kg of caprylic anhydride and 6 g of tin oxalate had been added, the mixture was stirred at 195° C. for 10 hours, in the course of which water was removed by distillation. On completion of reaction and removal of the catalyst, the excess acid was removed under reduced pressure. The product obtained was a clear bright yellow oil.

EXAMPLE 2

Use of the product fully esterified with caprylic anhydride as a hydraulic fluid The product obtained in example 1 from the esterification reaction of D-sorbitol and D-mannitol with caprylic anhydride (n-C8) was tested as a base fluid for hydraulic oils. The product obtained in example 1 was additized with additives typical of hydraulic oils, such as phenolic and aminic antioxidants, phosphorus/sulfur extreme pressure/antiwear additives, corrosion inhibitors and a foam inhibitor. Subsequently, the properties of this mixture were investigated with a view to its suitability as a hydraulic fluid. The following results were obtained:

Kinematic viscosity at 40° C.: 36 $mm^2/s$

Pour point: −30° C. The measurement was in accordance with DIN ISO 3016. This value is to be regarded as good.

Long-term cold stability: still free-flowing after 3 days at −25° C. This value is to be regarded as good.

Air release capability at 50° C.: 3 minutes. The measurement was in accordance with DIN 51381. This value is to be regarded as good.

Demulsification capability: 25 minutes at 50° C. The measurement was in accordance with DIN 51599. This value is to be regarded as good.

Load-bearing capability/wear behavior: still free of damage at load stage 11 in the FZG A/8.3/90 test method. The wear scar diameter was 0.31 mm in a four-ball apparatus to DIN 51350. The values are to be regarded as very good.

Aging stability: 1900 hours in the turbine oil stability test without the addition of water until an acid number of 2 mg KOH/g has been attained.

COMPARATIVE EXAMPLE 1

Testing of fully esterified glycerol for suitability as a hydraulic fluid

The base fluid used was glycerol which had been fully esterified with a mixture of caprylic acid and caproic acid. The resulting product was additized with phenolic and aminic antioxidants, phosphorus/sulfur extreme pressure/antiwear additives, corrosion inhibitors and a foam inhibitor, and the additives were identical to the additives in example 2. The following properties were determined for this base fluid:

Kinematic viscosity at 40° C.: 15 $mm^2/s$. For most applications, this value is too low.

Pour point: −10° C. The measurement was in accordance with DIN ISS 3016. This value is not low enough for most applications, especially in colder climates.

Long-term cold stability: after 3 days at −25° C., no longer free-flowing. This value is unacceptable for applications in cold climates.

Air release capability at 50° C.: 6 minutes. The measurement was in accordance with DIN 51381. The value is to be regarded as moderately good.

Demulsification capability: 20 minutes at 50° C. The measurement was in accordance with DIN 51599. The value is to be regarded as good.

Load-bearing capability/wear behavior: still free of damage at load stage 10 in the FZG A/8.3/90 test method. Wear scar diameter 0.35 mm in a four-ball apparatus to DIN 51350. Both values are to be regarded as moderately good.

Aging stability: 1200 hours in the turbine oil stability test without the addition of water until an acid number of 2 mm KOH/g has been attained. This value is to be regarded as moderately good.

COMPARATIVE EXAMPLE 2

Testing of glycerol which had been esterified with sunflower oil fatty acid with a view to suitability as a hydraulic fluid The base fluid used was glycerol which had been fully esterified with sunflower oil fatty acid (high oleic quality, oleic acid fraction 80%). The glycerol ester was additized with phenolic and aminic antioxidants, phosphorus/sulfur extreme pressure/antiwear additives, corrosion inhibitors and a foam inhibitor. The additives were identical to those used in example 2. For the base fluid obtained in this way, the following properties were determined:

Kinematic viscosity at 40° C.: 38 mm$^2$/s

Pour point: −10° C. The measurement was in accordance with DIN ISO 3016. This value is not low enough for most applications, especially in colder climates.

Long-term cold stability: After three days at −25° C., no longer free-flowing. This value is unacceptable for use in cold climates.

Air release capability at 50° C.: 4 minutes. The measurement was in accordance with DIN 51381. The value is to be regarded as good.

Demulsification capability: 22 minutes at 50° C. The measurement was in accordance with DIN 51599. The value is to be regarded as good.

Load-bearing capability/wear behavior: still without damage at highest load stage (12) in the FZG A/8.3/90 test method. Wear scar diameter 0.31 mm in the four-ball apparatus to DIN 51350. Both values are to be regarded as very good.

Aging stability: 450 hours in the turbine oil stability test without the addition of water until an acid number of 2 mm KOH/g has been attained. This value is to be regarded as poor.

What is claimed is:

1. A method for making a base fluid for a rapidly biodegradable hydraulic fluid, said base fluid having low cold viscosity, wherein the method comprises the steps of:
   (a) forming a carbohydrate mixture comprised of mannitol and sorbitol; and
   (b) esterifying said carbohydrate mixture with at least one selected from the group consisting of a $C_2$ to $C_{24}$ monocarboxylic acid, a $C_2$ to $C_{24}$ monocarboxylic acid derivative and mixtures thereof to convert said carbohydrate mixture to a polyester mixture, such that at least 75% of all free hydroxyl groups in the carbohydrate mixture are esterified, wherein the polyester mixture is said base fluid.

2. The method as claimed in claim 1, wherein the carbohydrate mixture is esterified with a $C_4$ to $C_{18}$ monocarboxylic acid.

3. The method as claimed in claim 1, wherein the carbohydrate mixture is esterified with the $C_2$ to $C_{24}$ monocarboxylic acid and wherein the monocarboxylic acid is selected from the group consisting of acetic acid, butyric acid, isobutanoic acid, valeric acid, isovaleric acid, caproic acid, enanthic acid, caprylic acid, 2-ethylcaproic acid, pelargonic acid, capric acid, isostearic acid, lauric acid, myristic acid, myristoleic acid, palmitic acid, palmitoleic acid, stearic acid, oleic acid, elaidic acid, ricinoleic acid, linoleic acid, linolenic acid, eleostearic acid, arachic acid, behenic acid, erucic acid and mixtures thereof.

4. The method as claimed in claim 1, wherein the carbohydrate mixture is esterified with said monocarboxylic acid derivative, and wherein the derivative is an anhydride, a mixed anhydride, an alkyl ester or a carbonyl chloride.

5. The method as claimed in claim 1, wherein substantially all free hydroxyl groups in the carbohydrate mixture are esterified.

6. The method as claimed in claim 1, wherein the carbohydrate mixture is esterified in the presence of a catalyst.

7. The method as claimed in claim 6, wherein the catalyst is one selected from the group consisting of a transition metal compound, a mineral acid, an organic acid, an acidic ion exchanger, an alkali metal salt, a zeolite and mixtures thereof.

8. The method as claimed in claim 7, wherein the catalyst is the transition metal compound and wherein the transition metal compound is selected from among salts, oxides and alkyls of Sn, Ti and Zn/Cu.

9. The method as claimed in claim 7, wherein the catalyst is the mineral acid and wherein the mineral acid is selected from among HCl, $H_2SO_4$ and $H_3PO_4$.

10. The method as claimed in claim 7, wherein the catalyst is the organic acid and wherein the organic acid is selected from among p-toluenesulfonic acid, methanesulfonic acid and sulfosuccinic acid.

11. The method as claimed in claim 7, wherein the catalyst is the alkali metal salt and wherein the alkali metal salt is selected from among hydroxides, carbonates, methoxides and ethoxides of sodium and of potassium.

12. The method as claimed in claim 7, wherein the catalyst is p-toluenesulfonic acid or a tin oxalate catalyst.

13. The method as claimed in claim 1, wherein the esterification is effected in at least one solvent.

14. The method as claimed in claim 13, wherein the solvent is an organic solvent.

15. The method as claimed in claim 14, wherein the solvent is selected from among toluene, DMSO, pyridine and DMF.

16. The method as claimed in claim 1, wherein the esterification occurs at a temperature of from 120° C. to 280° C.

17. The method as claimed in claim 1, wherein a ratio of hydroxyl groups to carboxylic acid groups in the esterification reaction is from 1:1 to 1:10.

18. The method as claimed in claim 1, wherein the reaction time for the esterification reaction is from 2 to 36 hours.

19. The method as claimed in claim 1, wherein the base fluid has a kinematic viscosity at 40° C. of from 20 to 120 mm$^2$/s.

20. The method as claimed in claim 1, wherein the base fluid has a long-term cold stability that renders it still free flowing after 3 days at −25° C.

21. The method as claimed in claim 1, wherein the pour point of the base fluid is less than −25° C.

22. The method as claimed in claim 1, wherein the base fluid has a load bearing capability of at least load stage 10, determined in accordance with the FZG A/8.3/90 test method.

23. The method as claimed in claim 1, wherein the base fluid has an aging resistance such that more than 1800 hours are required in the turbine oil stability test without the addition of water to attain an acid number of 2 mg KOH/g.

* * * * *

UNITED STATES PATENT AND TRADEMARK OFFICE
CERTIFICATE OF CORRECTION

| | |
|---|---|
| PATENT NO. | : 7,524,798 B2 |
| APPLICATION NO. | : 10/486149 |
| DATED | : April 28, 2009 |
| INVENTOR(S) | : Markwart Kunz et al. |

It is certified that error appears in the above-identified patent and that said Letters Patent is hereby corrected as shown below:

On the Title Page:

Item (54), change the title from "USE OF A POLYSTER COMPOSITION AS A HYDRAULIC FLUID" to --USE OF A POLYESTER COMPOSITION AS A HYDRAULIC FLUID--

Replace Item (73) Assignee with:
Item --(73) Assignees: SÜDZUCKER AKTIENGESELLSCHAFT MANNHEIM/OCHSENFURT, Mannheim (DE); FUCHS PETROLUB AG, Mannheim (DE)--

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,524,798 B2
APPLICATION NO. : 10/486149
DATED : April 28, 2009
INVENTOR(S) : Markwart Kunz et al.

It is certified that error appears in the above-identified patent and that said Letters Patent is hereby corrected as shown below:

On the Title Page, Item (54) and Column 1, lines 1 and 2,

Change the title from "USE OF A POLYSTER COMPOSITION AS A HYDRAULIC FLUID" to --USE OF A POLYESTER COMPOSITION AS A HYDRAULIC FLUID--

Replace Item (73) Assignee with:
Item --(73) Assignees: SÜDZUCKER AKTIENGESELLSCHAFT MANNHEIM/OCHSENFURT, Mannheim (DE); FUCHS PETROLUB AG, Mannheim (DE)--

This certificate supersedes the Certificate of Correction issued July 14, 2009.

Signed and Sealed this

Eighteenth Day of August, 2009

David J. Kappos
*Director of the United States Patent and Trademark Office*